United States Patent [19]
Shimp et al.

[11] Patent Number: 4,931,545
[45] Date of Patent: Jun. 5, 1990

[54] FLAME RETARDANT POLYCYANATE ESTER BLEND

[75] Inventors: David A. Shimp, Prospect; Steven J. Ising, Louisville, both of Ky.

[73] Assignee: Hi-Tek Polymers, Inc., Jeffersontown, Ky.

[21] Appl. No.: 347,251

[22] Filed: May 3, 1989

[51] Int. Cl.$^5$ .............................................. C08G 83/00
[52] U.S. Cl. .................................... 528/422; 528/423
[58] Field of Search ............................... 528/422, 423

[56] References Cited
U.S. PATENT DOCUMENTS
4,745,215  5/1988  Cox et al. .......................... 528/422

Primary Examiner—Harold D. Anderson
Attorney, Agent, or Firm—Herbert P. Price

[57] ABSTRACT

Flame retardant thermoset compositions having excellent water absorption resistance, caustic resistance, and low dielectric constants are made from blends of the dicyanate ester of 4,4'-(hexafluoroisopropylidene) bisphenol and a different polycyanate ester of a polyhydric phenol.

17 Claims, No Drawings

FLAME RETARDANT POLYCYANATE ESTER BLEND

BACKGROUND OF THE INVENTION

The field of art to which this invention pertains is aryl cyanate esters, i.e., cyanic acid esters of polyhydric phenols.

Industry needs lighter, stronger and more resistant materials to be used in place of the materials used today. For example, the aerospace industry is devoting considerable effort to utilizing structural composites in place of metals. Structural composites based on thermoplastic and thermoset resins and glass or carbon fibers have been and are being used successfully in many parts of military and commercial aircraft. The electronics industry needs materials which have better moisture and heat resistance and lower dielectric constants then those which have been used in the past. Thermoset resins finding use in such applications are based on epoxy resins, bismaleimide resins, and cyanate ester resins.

Materials which are flame resistant or fire retardant are needed for many of the old and new applications. Most cyanate esters, epoxy resins and bismaleimide resins are not flame resistant. The addition of other materials, such as phosphorus or bromine containing resins, is needed to obtain this property. Such modifications decrease thermal stability and glass transition temperature, and can adversely affect elevated temperature modulus, and dielectric loss properties as well as generate ionic species which cause metal corrosion.

Thermoset resins based on the dicyanate ester of 4,4'-(hexafluoroisopropylidene)bisphenol are inherently flame retardant and self-extinguishing. However, such resins have poor long term moisture resistance and poor caustic resistance. Structures based on such resins will absorb moisture from air having a relative humidity as low as 50 percent. When suddenly heated, the moisture can be expelled under forces sufficient to fracture the structure. The absorbed moisture also plasticizes the resin, thereby lowering its Tg and reducing the temperature at which it retains its stiffness.

In the processing of electronic parts, e.g., printed circuit boards, the parts are often subjected to aqueous caustic baths. Structures made with a matrix of the cyanate ester of 4,4'-(hexafluoroisopropylidene) bisphenol are degraded when contacted with the caustic.

Dicyanate esters made from 2,2-bis(4'-hydroxyphenyl-1,1,1, 3,3,3-hexafluoropropane) are disclosed in U.S. Pat. No. 4,157,360. Such dicyanate esters, referred to as 4,4'-(hexafluoroisopropylidene) bisphenol dicyanate, are described in detail in U.S. Pat. No. 4,745,215. Such dicyanate ester resins are said to have low dielectric constants, very low moisture absorption, good thermal stability and a high glass transition temperature (Tg). In addition, such resins are said to readily form alloys with both thermoplastic and thermosetting resins thereby allowing them to be used for a variety of electronic applications, i.e., packaging or circuit boards.

There is a need for cyanate ester compositions which not only are flame resistant but have moisture resistant and caustic resistant properties superior to the dicyanate ester of 4,4'-hexafluoroisopropylidene) bisphenol.

SUMMARY OF THE INVENTION

This invention is directed to blends of polycyanate esters of polyhydric phenols. In one aspect, this invention pertains to curable blends of polycyanate esters of polyhydric phenols. In another aspect, this invention relates to cured compositions based on blends of polycyanate esters of polyhydric phenols.

The curable compositions of this invention are made from a blend of (A) the dicyanate ester of 4,4'-(hexafluoroisopropylidene) bisphenol and (B) a different polycyanate ester of a polyhydric phenol. When properly cured, the blended polycyanate esters have flame retardant properties equal to those of 4,4'-(hexafluoroisopropylidene) bisphenol, and moisture and caustic resistance properties which are superior to the individual polycyanate esters components of the blend when cured alone.

The cured compositions of this invention are particularly useful in "high tech" electronic circuitry and in structural composites used in supersonic aircraft.

BACKGROUND OF THE INVENTION

Polycyanate esters of polyhydric phenols are well known compositions which are made by reacting a cyanogen halide with a polyhydric phenol in the presence of an acid acceptor, i.e., a base. This reaction is described in such patents as U.S. Pat. Nos.3,553,244 and 4,089,393, which are hereby incorporated by reference.

The dicyanate ester of 4,4'-(hexafluoroisopropylidene) bisphenol is described in detail in U.S. Pat. No. 4,745,215 which is hereby incorporated by reference. This dicyanate ester when refined to a purity exceeding 99 mole percent is a white crystalline powder, having a melting point of 86° C., and a density of 1.497 g/cc. The theoretical molecular weight of the pure compound is 386 and the fluorine content is 29.5 percent.

The other polycyanate esters of polyhydric phenols useful in this invention are derived from such polyhydric phenols as resorcinol, p,p'-dihydroxydiphenyl, o,p'-dihydroxydiphenyl methane, p,p'-dihydroxydiphenyl propane, p,p'-dihydroxydiphenyl sulfone, p,p'-dihydroxydiphenyl sulfide, p,p'-dihydroxydiphenyl oxide, 4,4'-methylenebis(2,6-dimethyl phenol), p,p',p"-trihydroxy triphenyl ethane, dihydroxynaphthalene and novolac resins which contain more than 2 phenol moieties per molecule. Preferred cyanate esters are those derived from dihydric phenols having substituents ortho to the hydroxyl group and cyanate esters of dihydric phenols which contain no substituents ortho to the hydroxyl group. Examples of the ortho substituted dihydric phenols are bis(4-hydroxy-3,5-dimethylphenyl) methane, bis(4-hydroxy-3,5- dimethylphenyl., propane, bis(4-hydroxy-3,5-dimethylphenyl) ether, bis(4-hydroxy-3,5-dimethylphenyl)-1,1-ethane, and bis(4-hydroxy-3,5-dimethylphenyl) sulfide. The preferred dihydric phenol from this group is bis(4-hydroxy-3,5'-dimethyl phenyl) methane.

The dihydric phenols which contain no ortho substituents include bis(4-hydroxyphenyl)-2,2-propane, bis(4-hydroxyphenyl) ether, and bis(4-hydroxyphenyl) sulfide. The preferred dihydric phenol from this group is bis(4-hydroxyphenyl)-2,2-propane (Bisphenol A).

A particularly preferred dicyanate ester composition useful in this invention for blending with the fluorine containing dicyanate ester is a blend of the dicyanate ester of bis(4-hydroxy-3,5-dimethylphenyl) methane and bis(4-hydroxyphenyl)-2,2-propane described in U.S. Pat. No. 4,740,584 which is hereby incorporated by reference.

The compositions of this invention are made by blending the polycyanate esters in the amounts of about 15 to 85 weight percent of the flourine containing dicyanate ester and about 85 to about 15 weight percent of the different cyanate ester. Preferred blends contain about 35 to about 65 weight percent of the fluorine containing dicyanate ester and about 65 to about 35 weight percent of the different cyanate esters.

The blends of polycyanate esters can be used as is, can be blends of partially trimerized prepolymers of the fluorine containing dicyanate ester and partially trimerized prepolymers of the different polycyanate ester, or can be partially co-trimerized prepolymers of the fluorine containing dicyanate ester and the different polycyanate ester. Blends of the polycyanate ester monomers with partially trimerized prepolymers can also be used.

Prepolymers are amorphous in form and are somewhat easier to use in prepregging operations than the crystalline or semi-crystalline unpolymerized blends. Prepolymers are made by heating the polycyanate ester or a blend of polycyanate esters with or without catalysts at a temperature of about 140° C. to about 240° C. for a time sufficient to cyclotrimerize from about 5 to about 60 percent of the cyanate functional groups and, preferably, about 15 to about 50 percent of the cyanate functional groups. Useful prepolymers possess melt viscosities ranging from about 1,000 cps. at 50° C. up to 10,000 cps. at 150° C. Catalysts which can be used in preparing the prepolymers are mineral or Lewis acids, bases such as alkali metal hydroxides, alkali metal alcoholates or tertiary amines, salts such as sodium carbonate or lithium chloride, or active hydrogen containing compounds, such as bisphenols and monophenols. It is preferred to conduct the prepolymerization reaction without a catalyst, utilizing only heat followed by thermal quenching, in the manner taught by British No. 1,305,762 which is hereby incorporated by reference.

Cyanate ester content can be determined quantitatively by infrared analysis or by "residual heat of reaction" using a differential scanning calorimeter. The percent trimerization is calculated by the formula:

$$\text{Percent Trimerization} = 100 \left[ \frac{\text{Wt/OCN Monomer}}{\text{Wt/OCN Prepolymer}} \times 100 \right]$$

wherein Wt/OCN is the equivalent weight per cyanate group.

Refractive index is directly related to the percent trimerization. A plot of refractive indices, taken at the same temperature, versus percent trimerization is linear. The slope of the plotted line will vary with the chemical composition of the particular cyanate ester or mixture being prepolymerized. By using these plots, the refractive index can be used to monitor the rate of reaction and the extent of the cyclotrimerization reaction.

The compositions of this invention can be cured by heat alone but are preferably cured by the use of an active hydrogen, or metal coordination class catalyst or mixture of both plus heat. Such curing catalysts include those described above which are used in preparing prepolymers. Additional catalysts are those described in U.S. Pat. Nos. 3,962,184, 3,694,410 and 4,026,213 which are hereby incorporated by reference. Examples of such catalysts include zinc octoate, manganese octoate, zinc stearate, cobalt stearate, copper acetylacetonate, phenol, catechol, triethylenediamine and chelates of iron, cobalt, zinc, copper, manganese and titanium with bidentate ligands such as catechol. Such catalysts are used in the amounts of about 0.001 to about 20 parts by weight per 100 parts by weight cf the cyanate ester blend. A preferred catalyst system is that described in U.S. Pat. No. 4,604,452. Such catalysts are liquid solutions of a metal carboxylate and an alkylphenol, e.g., zinc naphthenate and nonylphenol. These catalyst are used in the amounts of about 0.001 to about 0.5 part by weight of metal and about 1 to about 20 parts by weight of alkylphenol per 100 parts by weight of cyanate ester blend.

The compositions of this invention are cured by heating at elevated temperatures for a time sufficient to obtain a complete cure, i.e., until at least about 80 percent of the cyanate functional groups are cyclotrimerized. The curing reaction can be conducted at one temperature or can be conducted by heating in steps. If conducted at one temperature, the temperature will vary from about 250° F. to about 450° F. When conducted by stepwise heating, the first step, or gelation step, is performed at a room temperature of about 150° F. to about 350° F. The curing step is conducted at a temperature of about 300° F. to about 450° F., and the optional post-curing step is conducted at a temperature of about 400oF. to about 550oF The overall curing reaction will take about 5 minutes to about 8 hours.

The compositions of this invention, particularly blends of the prepolymers, are combined with fibrous reinforcements to make structural composites and electrical grade laminates. The fibrous reinforcements can be in the form of woven fabrics, non-woven mats or sheets, and unidirectional tows. They are made from glass fibers, e.g., E-glass, D-glass, and S-glass, aramide fibers, quartz fibers, and carbon or graphite fibers. Generally, the composites and laminates contain from about 15 to about 65 volume percent fiber.

Cured compositions made from the blends of this invention have flame resistant, strength, and electrical properties which are substantially the same as or intermediate to the properties of each of the components of the blend when cured alone. However, the water absorption properties and the Tg after exposure to water, as well as the resistance to aqueous caustic, of the blends of this invention are superior to the same properties of each of the components when cured alone.

The water absorption of the cured compositions of this invention, when determined on a casting having the dimensions of 0.5 inch by 2 inches by 0.125 inch, is equal to or less than 1 weight percent based on the weight of the casting after 13 hours immersion in boiling water (100° C).

The caustic resistance, i.e., the resistance to etching, of the cured compositions of this invention is determined on castings having the dimensions of 0.5 inch by 2 inches by 0.125 inch by immersing the castings in aqueous caustic solution (20 weight percent NaOH) at 50° C. Usually, the castings show a gain in weight initially due to their absorbing water followed by a loss in weight due to etching and decomposition of the surface of the casting. The cured compositions of this invention when subjected to the caustic resistance test, show no net weight loss after 100 hours immersion.

The following examples describe the invention in more detail. Parts and percentages are parts and percentages by weight unless otherwise designated. The polycyanate esters of polyhydric phenols used in the following examples are identified as follows:

FluoroCy-dicyanate ester of 4,4'-(hexafluoroisopropylidene) bisphenol having a degree of purity greater than 99 mole percent and a melting point of 86° C.

MethylCy-dicyanate ester of bis(4-hydroxy-3,5-dimethylphenyl) methane having a degree of purity greater than 99 mole percent and a melting point of 106° C.

BadCy-dicyanate ester of bis(4-hydroxyphenyl)-2,2-propane having a degree of purity greater than 99 mole percent and a melting point of 79° C.

EXAMPLE 1

Castings were prepared from FluoroCy, MethylCy and blends of FluoroCy and MethylCy by the following procedure: the cyanate ester monomers or blends of monomers were melted by heating to a temperature of 90° C. to 110° C. To the molten ester was added a catalyst solution of zinc naphthenate and nonyl phenol. The formulated melts were vacuum deaired and cast into ¼ inch thick aluminum plate molds with ⅛ inch thick Teflon gaskets and treated with silicone mold release. The castings were gelled at 104 to 150° C. and then were cured 1 hour at 177° C. plus 1 hour at 210° C. plus 2 hours at 250° C. The cured castings were cut into test bars and were tested for certain properties.

Heat deflection temperatures were determined using the procedure of ASTM-D648.

An Omnitherm Analyzer was used at a heatup rate of 10° C. per minute for TGA measurements of first onset of decomposition in air. This analyzer was also used for DMA measurements of Tg by noting the temperature at which the loss modulus peaks.

Flammability resistance was measured by UL94, a vertical burn test.

Electrical measurements were made on a Genrad 16987B Digibridge equipped with an LD-3 cell and using the two fluid method (air and DC-200, 1 cs).

The components of the castings and the test results are shown in Table 1.

TABLE 1

| Cured Properties of Cyanate Esters | | | | | |
|---|---|---|---|---|---|
| Composition (parts) | A | B | C | D | E |
| FluoroCy | 100 | 65 | 50 | 35 | |
| MethylCy | | 35 | 50 | 65 | 100 |
| Nonylphenol | 2 | 2 | 2 | 2 | 2 |
| Zinc Naphthenate, 8% Zn | 0.125 | 0.125 | 0.125 | 0.14 | 0.22 |
| Cured State Properties | | | | | |
| HDT °C. | 238 | 231 | 233 | 230 | 242 |
| Tg (DMA) °C. | | | | | |
| Dry | 270 | 257 | 257 | 251 | 252 |
| 200 Hour H₂O Boil | 173 | 248 | 241 | 245 | 244 |
| TGA Onset Temp, °C. | 431 | 426 | 420 | 418 | 403 |
| Flexure Strength, ksi | 17.2 | 16.4 | 20.6 | 18.5 | 23.3 |
| Flexure Modulus, msi | 0.49 | 0.48 | 0.46 | 0.44 | 0.42 |
| Flexure Strain, % | 4.5 | 3.4 | 4.9 | 4.6 | 6.6 |
| % H₂O Absorption @ 100° C. | | | | | |
| 24 hours | 0.73 | 0.66 | 0.60 | 0.77 | 0.83 |
| 135 hours | 1.65 | 0.87 | 0.86 | 0.85 | 1.06 |
| 208 hours | 1.76 | 0.93 | 0.94 | 0.92 | 1.10 |
| Flammability Seconds to extinguish | | | | | |
| 1st ignition | 0 | 0 | 0 | 0 | 20 |
| 2nd ignition | 0 | 0 | 0 | 3 | 14 |
| Rating | V-0 | V-0 | V-0 | V-0 | V-1 |
| Dk @ 1 MHz | | | | | |
| Dry | 2.66 | 2.69 | 2.70 | 2.72 | 2.76 |
| 48 hours H₂O Boil | 3.03 | 2.98 | 2.95 | 2.99 | 3.05 |
| Df @ 1 MHz | | | | | |
| Dry | 0.003 | 0.003 | 0.003 | 0.003 | 0.002 |
| 48 hours H₂O Boil | 0.010 | 0.010 | 0.010 | 0.010 | 0.009 |
| Specific Gravity | 1.437 | 1.324 | 1.268 | 1.218 | 1.117 |

EXAMPLE 2

Using the same procedure described in Example 1, additional castings of cyanate esters were made and tested. The gel time for the MethylCy casting (A) was 120 minutes at 250° F. plus 60 minutes at 300° F. The gel time for the 75 percent MethylCy, 25 percent FluoroCy casting (B) was 120 minutes at 250° F. plus 30 minutes at 300° F. The gel times for the other castings at 250° F. were 80 minutes (C), 60 minutes (F) and 65 minutes (G). All castings were cured for 1 hour at 350° F., 1 hour at 420° F. and 2 hours at 482° F. Weight increases for test bars immersed in caustic solution derive from water absorption while weight loss signifies resin saponifications and surface etching.

TABLE II

| Cured Properties of Cyanate Esters | | | | | | | |
|---|---|---|---|---|---|---|---|
| Composition (parts) | A | B | C | D | E | F | G |
| MethylCy | 160 | 120 | 104 | 80 | 56 | — | 52 |
| FluoroCy | — | 40 | 56 | 80 | 104 | 160 | 80 |
| BadCy | — | — | — | — | — | — | 28 |
| Nonylphenol | 3.2 | 3.2 | 3.2 | 3.2 | 3.2 | 3.2 | 3.2 |
| Zn Naphthenate, % Zn | 0.3 | 0.23 | 0.23 | 0.2 | 0.2 | 0.2 | 0.2 |
| Casting Properties | | | | | | | |
| HDT °C. Dry | 211 | 218 | 220 | 223 | 231 | 238 | 251 |
| 64 hours H₂O Boil | 210 | 214 | 214 | 218 | 222 | 160 | 232 |
| 208 hours H₂O Boil | 207 | 209 | 211 | 209 | 213 | 130 | 204 |
| Tg (DMA) °C. | | | | | | | |
| Dry | 246 | 251 | 251 | 257 | 257 | 270 | 277 |
| 200 hours H₂O Boil | 240 | 244 | 245 | 241 | 248 | 173 | 242 |
| Tg (TMA) °C. | 222 | 265 | 265 | 276 | 276 | 261 | 278 |
| Flexure Str., ksi | 13.7 | 13.6 | 12.4 | 20.6 | 16.4 | 14.8 | 14.3 |
| Flexure Mod., ksi | 0.43 | 0.58 | 0.35 | 0.46 | 0.48 | 0.34 | 0.58 |
| Flexure Strain, % | 3.03 | 2.34 | 3.72 | 4.86 | 3.44 | 4.60 | 2.45 |
| Specific Gravity | 1.127 | 1.203 | 1.218 | 1.268 | 1.324 | 1.437 | 1.277 |
| % H₂O Absorp 100° C. | | | | | | | |
| 24 hours | 0.83 | 0.73 | 0.77 | 0.60 | 0.66 | 0.73 | 0.80 |
| 48 hours | 0.81 | 0.72 | 0.83 | 0.71 | 0.73 | 1.20 | 0.84 |
| 64 hours | 1.10 | 0.84 | 0.82 | 0.78 | 0.86 | 1.51 | 0.88 |
| 135 hours | 1.06 | 1.01 | 0.85 | 0.86 | 0.87 | 1.65 | 1.05 |

TABLE II-continued

| Composition (parts) | Cured Properties of Cyanate Esters | | | | | | |
|---|---|---|---|---|---|---|---|
| | A | B | C | D | E | F | G |
| 208 hours | 0.93 | 0.92 | 0.92 | 0.94 | 0.93 | 1.76 | 1.17 |
| % Wt loss @ 450° F. in Air | | | | | | | |
| 24 hours | −0.37 | −0.38 | −0.31 | −0.31 | −0.32 | −0.52 | −0.35 |
| 72 hours | −0.49 | −0.54 | −0.47 | −0.44 | −0.47 | −0.58 | −0.46 |
| 308 hours | −1.06 | −1.37 | −1.30 | −1.46 | −1.50 | −6.91 | −1.43 |
| 642 hours | −1.76 | −2.44 | −2.39 | −2.82 | −2.85 | * | −2.72 |
| 978 hours | −2.35 | −3.34 | −3.28 | −3.74 | −3.80 | * | −3.57 |
| % Wt Change in 20% NaOH @ 50° C. | | | | | | | |
| 48 hours | +1.37 | +1.16 | +0.69 | +0.45 | +0.67 | −0.14 | +0.61 |
| 216 hours | +0.90 | +0.67 | +0.60 | +0.45 | +0.31 | −23.26 | +0.49 |
| 480 hours | −0.67 | −0.84 | +0.26 | +0.04 | −0.42 | * | +0.15 |
| 648 hours | −0.71 | −0.92 | +0.28 | −0.03 | −0.53 | — | +0.12 |
| 1152 hours | −0.82 | −1.12 | +0.23 | −0.24 | −0.81 | — | −0.03 |
| 1584 hours | −0.81 | −1.23 | +0.26 | −0.39 | −0.90 | — | −0.20 |

*disintegrated

EXAMPLE 3

To a suitable reactor were added 456 parts of FluoroCy. The refractive index (RI) of the cyanate ester measured at 110° C. was 1.4756. Heat was applied raising the temperature to 280° F. over a period of 1 hour and 40 minutes. The RI at 110° C. was 1.4759. The temperature was held at 280oF for 30 minutes and was then raised to 300° F. over 8 minutes. The temperature was held at 300° F. for 1 hour. At the end of this heating period, the RI was 1.4774. The temperature was then raised to 320° F. over 20 minutes, held at 320° F. for 1 hour, raised to 340° F. in 8 minutes, held at 340° F. for 1 hour, heated to 350° F. in 5 minutes and held at 350° F. for 1 hour. The RI at 110° C. after these heating periods was 1.4922. After cooling to room temperature and standing overnight, the reactor contents were heated to 320° F. over 40 minutes, were held at 320° F. for 30 minutes, heated to 340 ° F. in 5 minutes and were held at 340° F. for 45 minutes. The RI measured at 110° C. was 1.5026. The heating source was removed and the prepolymer was dissolved in 152 parts of methylethyl ketone. The solution had a Brookfield viscosity of 210 cps measured at 25° C. with a No. 3 spindle at 100 RPM. The solids content was 75 percent after heating 0.5 gram in an evaporating dish at 150° C. for 30 minutes. The Gardner color was 7 and the weight per gallon was 10.4 lbs. The weight per cyanate group (Wt/OCN) of the prepolymer was 284 which calculates to a conversion of cyanage groups to triazine rings of 32 percent.

EXAMPLE 4

To a suitable reactor were added 1040 parts of MethylCy and 560 parts of FluoroCy. Heat was applied raising the temperature to 225° F. The RI measured at 110° C. was 1.5105. The temperature was raised to 370° F. over a 2 hour period and was held at 370° F. for 1 hour and 30 minutes. The RI measured at 110° C. was 1.5278. The temperature was lowered to 348° F. over 30 minutes then to 315° F. in 30 minutes. The RI at 100° C. was 1.5332. The temperature was then raised to 340° F. in 30 minutes, and then to 356° F. in 30 minutes and then 356° F. in 1 hour. The RI at 110° C. was 1.5378. After 20 minutes at 355° C., the RI at 110° C. was 1.5392. A pill of the reaction products exhibited no crystallization tendencies when cooled. The heat source was removed and 862 parts of methylethyl ketone were added. The resulting co-prepolymer solution (65 weight percent MethylCy and 35 weight percent FluoroCy) had a viscosity of 78 cps measured at 25° C. with a No. 1 spindle at 50 RPM. The percent solids was 65.14, the weight per gallon 8.86 lbs, and the Gardner color 8.

EXAMPLE 5

Using the same procedure described in Example 3 and 4, 21.45 parts of MethylCy and 11.55 parts of BadCy were coprepolymerized to a maximum temperature of 380° F. The initial RI measured at 110° C. was 1.5282, the final RI was 1.5597. The resulting co-prepolymer (65 weight percent MethylCy and 35 weight percent BadCy) was dissolved in 17.77 parts of methylethyl ketone. The resulting solution, 65.35 percent solids had a Brookfield viscosity of 82 cps at 25° C., No 1 spindle at 50 RPM. The weight per gallon was 8.58 lbs and the Gardner color was 7. The Wt/OCN of the prepolymer was 243 indicating 41 percent conversion of cyanate groups to triazine rings.

EXAMPLE 6

Prepolymers were made from MethylCy and from BadCy using the procedure described in Examples 3 and 4. The MethylCy prepolymers at 65 percent solids in methylethyl ketone had a Brookfield viscosity at 25° C. of 85. The Gardner color was 12 and the weight per gallon was 8.58 pounds.

The BadCy prepolymer at 75 percent solids in methylethyl ketone had a Brookfield viscosity at 25° C. of 232 cps. The Gardner color was 6 and the weight per gallon was 9.05 lbs. The Wt/OCN of the prepolymer was 232, indicating a conversion of cyanate groups to triazine rings of 40 percent.

EXAMPLE 7

Laminates were prepared from prepolymer solutions and E-glass cloth using manganese octoate (50-100 ppm based on metal) and bisphenol A (1 phr) as catalysts. The prepolymer solutions and glass cloth were processed to B stage on a pilot treater, the gel conditions being 220-240 seconds at 171° C. Four ply laminates were prepared using a 1 hour at 177° C. press cure followed by a 3-5 hour at 225° C. oven cure. Laminates were made from the FluoroCy prepolymer of Example 3; the MethylCy prepolymer of Example 6; the co-prepolymer of Example 5; blends of the FluoroCy prepolymer and the MethylCy prepolymer; and blends of the FluoroCy prepolymer and the coprepolymer. Laminate compositions and properties are listed in Table 3.

TABLE 3

Cured Properties of Laminates of Cyanate Esters

| Composition (parts) | A | B | C | D | E | F |
|---|---|---|---|---|---|---|
| FluoroCy Prepolymer | 100 | | | 35 | 50 | 60 |
| MethylCy Prepolymer | | 100 | | 65 | | |
| Coprepolymer | | | 100 | | 50 | 40 |
| Resin Content wt % | 39.9 | 38.3 | 38.5 | 39.9 | 42.9 | 45.5 |
| Flammability Rating -UL-94 | V-0 | V-1 | V-1 | V-1 | V-0 | V-0 |
| Tg (DMA) °C. | 301 | 270 | 291 | | | |
| Tg (TMA) °C. | 274 | 235 | 255 | 247 | 244 | 257 |
| TGA Onset Temp °C. | 389 | 408 | 404 | 400 | 405 | 408 |
| Dk, 1 MHz @ 25° C. | 4.17 | 3.83 | 3.88 | 3.88 | | 3.77 |
| Df, 1 MHz @ 25° C. | .002 | .0014 | .0012 | .004 | .005 | .005 |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A curable composition comprising a blend of
   (A) a dicyanate ester of 4,4'-(hexafluoroisopropylidene) bisphenol and
   (B) a polycyanate ester different from A wherein A is present in the amount of about 20 to about 80 weight percent based on the weight of A and B.

2. The composition of claim 1 wherein A is present in the amount of about 35 to about 65 weight percent based on the weight of A and B.

3. The composition of claim 1 wherein B is selected from the group consisting of the dicyanate ester of bis(4-hydroxy-3,5-dimethylphenyl) methane and the dicyanate ester of bis(4-hydroxyphenyl)-2,2-propane, or mixtures thereof.

4. The composition of claim 1 which contains a polycyanate curing catalyst.

5. The composition of claim 4 wherein the catalyst is selected from the group consisting of active hydrogen class catalysts, metal coordination class catalysts, and mixtures thereof.

6. A curable composition comprising of blend of:
   (A) a partially trimerized prepolymer of 4,4'-(hexafluoroisopropylidene) bisphenol and
   (B) a partially trimerized prepolymer of a dicyanate ester different from (A), wherein A is present in the amount of about 20 to about 80 weight percent based on the weight of A and B.

7. The composition of claim 6 wherein the blend is comprised of a partial co-trimerized prepolyer of A and B.

8. The composition of claim 6 wherein about 5 to about 60 percent of the cyanate groups in the prepolymers are trimerized.

9. The composition of claim 8 wherein about 15 to about 50 percent of the cyanate groups are trimerized.

10. A cured composition obtained from a blend of:
    (A) a dicyanate ester of 4,4'-(hexafluoroisopropylidene) bisphenol and
    (B) a dicyanate ester different from A wherein A is present in the amount of about 20 to about 80 weight percent based on the weight of A and B.

11. The composition of claim 10 wherein A is present in the amount of about 35 to about 65 weight percent based on the weight percent of A and B.

12. The composition of claim 10 wherein B is selected from the group consisting of the dicyanate ester of bis(4-hydroxy-3,3-dimethylphenyl) methane and the dicyanate ester of bis(4-hydroxyphenyl)-2,2-propane, or mixtures thereof.

13. The composition of claim 10 which contains a polycyanate curing catalyst.

14. The composition of claim 13 wherein the catalyst is selected from the group consisting of active hydrogen class catalysts, metal coordination class catalysts, and mixtures thereof.

15. The cured composition of claim 10 in the form of a casting.

16. The cured composition of claim 10 in the form of a structural composite.

17. The cured composition of claim 10 in the form of an electrical grade laminate.

* * * * *